(12) United States Patent
Miller et al.

(10) Patent No.: US 9,179,533 B2
(45) Date of Patent: Nov. 3, 2015

(54) X-RAY TUBE ARC RIDE THROUGH

(75) Inventors: Lester D. Miller, Hudson, OH (US); Jaisingh Udaysingh Rajwade, Highland Heights, OH (US)

(73) Assignee: Koninklijke Philips N. V., Eindhoven (NL)

( * ) Notice: Subject to any disclaimer, the term of this patent is extended or adjusted under 35 U.S.C. 154(b) by 345 days.

(21) Appl. No.: 13/823,145

(22) PCT Filed: Sep. 14, 2011

(86) PCT No.: PCT/IB2011/054013
§ 371 (c)(1),
(2), (4) Date: Mar. 14, 2013

(87) PCT Pub. No.: WO2012/035500
PCT Pub. Date: Mar. 22, 2012

(65) Prior Publication Data
US 2013/0170626 A1    Jul. 4, 2013

Related U.S. Application Data

(60) Provisional application No. 61/383,843, filed on Sep. 17, 2010.

(51) Int. Cl.
| | |
|---|---|
| H05G 1/26 | (2006.01) |
| A61B 6/03 | (2006.01) |
| G06T 11/00 | (2006.01) |
| G06F 17/00 | (2006.01) |
| H05G 1/54 | (2006.01) |

(52) U.S. Cl.
CPC ............... *H05G 1/265* (2013.01); *A61B 6/032* (2013.01); *G06F 17/00* (2013.01); *G06T 11/005* (2013.01); *H05G 1/54* (2013.01)

(58) Field of Classification Search
CPC ........ A61B 6/032; A61B 6/102; C08G 18/10; C09D 163/00; G06F 17/00; G06T 11/005; H05G 1/06; H05G 1/20; H05G 1/54; H05G 1/265; Y10S 378/901
USPC ......... 378/101, 105, 106, 107, 117, 118, 162, 378/901
See application file for complete search history.

(56) References Cited

U.S. PATENT DOCUMENTS

| | | | |
|---|---|---|---|
| 5,347,571 | A | 9/1994 | Furbee et al. |
| 5,400,387 | A * | 3/1995 | Gard et al. ................. 378/207 |
| 6,449,337 | B1 | 9/2002 | Honda et al. |
| 2003/0185427 | A1* | 10/2003 | Hsieh et al. ................. 382/131 |
| 2005/0047551 | A1* | 3/2005 | Dong et al. ................. 378/204 |
| 2006/0245538 | A1 | 11/2006 | Bernhardt et al. |
| 2009/0097611 | A1 | 4/2009 | Nishide et al. |

FOREIGN PATENT DOCUMENTS

| | | |
|---|---|---|
| JP | 2010131215 A | 6/2010 |
| WO | 0243451 A2 | 5/2002 |

\* cited by examiner

*Primary Examiner* — Irakli Kiknadze
*Assistant Examiner* — Julio M Duarte-Carvajalino

(57) ABSTRACT

A method includes identifying projection data generated during an x-ray tube arc event, determining x-ray tube voltages for data points of the identified projection data, correcting the identified data points based on the determined x-ray tube voltages for the data points, and reconstructing projection data that includes projection data generated during non x-ray tube arc events and the corrected projection data, and a system includes a projection data processor (116) that corrects projection data corresponding to data acquired during an x-ray tube arc event.

17 Claims, 4 Drawing Sheets

X-RAY TUBE ARC RIDE THROUGH

CROSS REFERENCE TO RELATED APPLICATIONS

This is a national filing of PCT application Ser. No. PCT/IB2011/054013, filed Sep. 14, 2011, published as WO 2012/035500 A1 on Mar. 22, 2012, which claims the benefit of U.S. provisional application Ser. No. 61/383,843 filed Sep. 17, 2010, which is incorporated herein by reference.

DESCRIPTION

The following generally relates to x-ray tubes and in particular to utilizing data acquired during an x-ray tube arc event and is described with particular application to computer tomography (CT) scanners. The following is also amenable to other imaging modalities such as Radiography and/or other imaging modalities where an x-ray tube is used in connection with radiation sensitive detector. Furthermore, the foregoing applies to medical and/or non-medical systems.

X-ray tube arcing is a condition where the dielectric impedance of the vacuum gap is compromised, and the x-ray tube voltage and/or current cannot be maintained. The output and quality during an x-ray tube arc cannot be maintained, and typically will result in image artifacts. It has always been an extreme challenge to design a high power x-ray tube that does not arc. Typically, there is a trade off between pushing the power of an x-ray tube to its limits and the inherent tendency of the tube to exhibit arcing behavior.

The high voltage systems of past computed tomography (CT) scanners had relatively slow voltage rise times and thus recoveries from a tube arc. One approach for handling x-ray tube arcing with such systems is described in detail in U.S. Pat. No. 5,347,571, which describes an approach using an arc-suppressor. This device allowed the voltage across the tube to collapse during an arc in such a way that the x-ray tube could recover and continue on. Unfortunately, the x-ray tube would only be able to recover about 80% of the time.

With the advances in technology a new type of high voltage generator was developed that has a very fast high voltage rise time. This opened up the door for new ways to handle tube arcing as it was now possible to shut off the generator for an arc and turn the high voltage back on with the whole cycle taking place in about one millisecond (1 mS). With this technology the voltage could be removed from the x-ray tube long enough for the tube to recover, thus eliminating many premature terminations of CT studies.

Unfortunately, x-ray tubes are still susceptible to arcing, and the data acquired during an arc generally is ignored for reconstruction and replaced by interpolated data from a valid point before the arc to a valid data point after the arc. Furthermore, turning off the high voltage and turning it back on has some inherent limitations. The off time is fixed by the mean free time for the breakdown event to quench, and the time to ramp the high voltage back up is limited by the rise time of the high-voltage power supply.

Aspects of the present application address the above-referenced matters and others.

According to one aspect, a method includes identifying projection data generated during an x-ray tube arc event, determining x-ray tube voltages for data points of the identified projection data, correcting the identified data points based on the determined x-ray tube voltages for the data points, and reconstructing projection data that includes projection data generated during non x-ray tube arc events and the corrected projection data.

According to another aspect, a system includes a projection data processor that corrects projection data corresponding to data acquired during an x-ray tube arc event.

According to another aspect, a method of correcting data collected during an x-ray tube arc includes identifying the tube arc, establishing a relationship between x-ray attenuation values and x-ray tube voltage, determining one or more x-ray tube voltages at different time periods during the tube arc, and using the relationship to determine a correction values for x-ray attenuation values during the x-ray tube arc.

The invention may take form in various components and arrangements of components, and in various steps and arrangements of steps. The drawings are only for purposes of illustrating the preferred embodiments and are not to be construed as limiting the invention.

Figure 1:
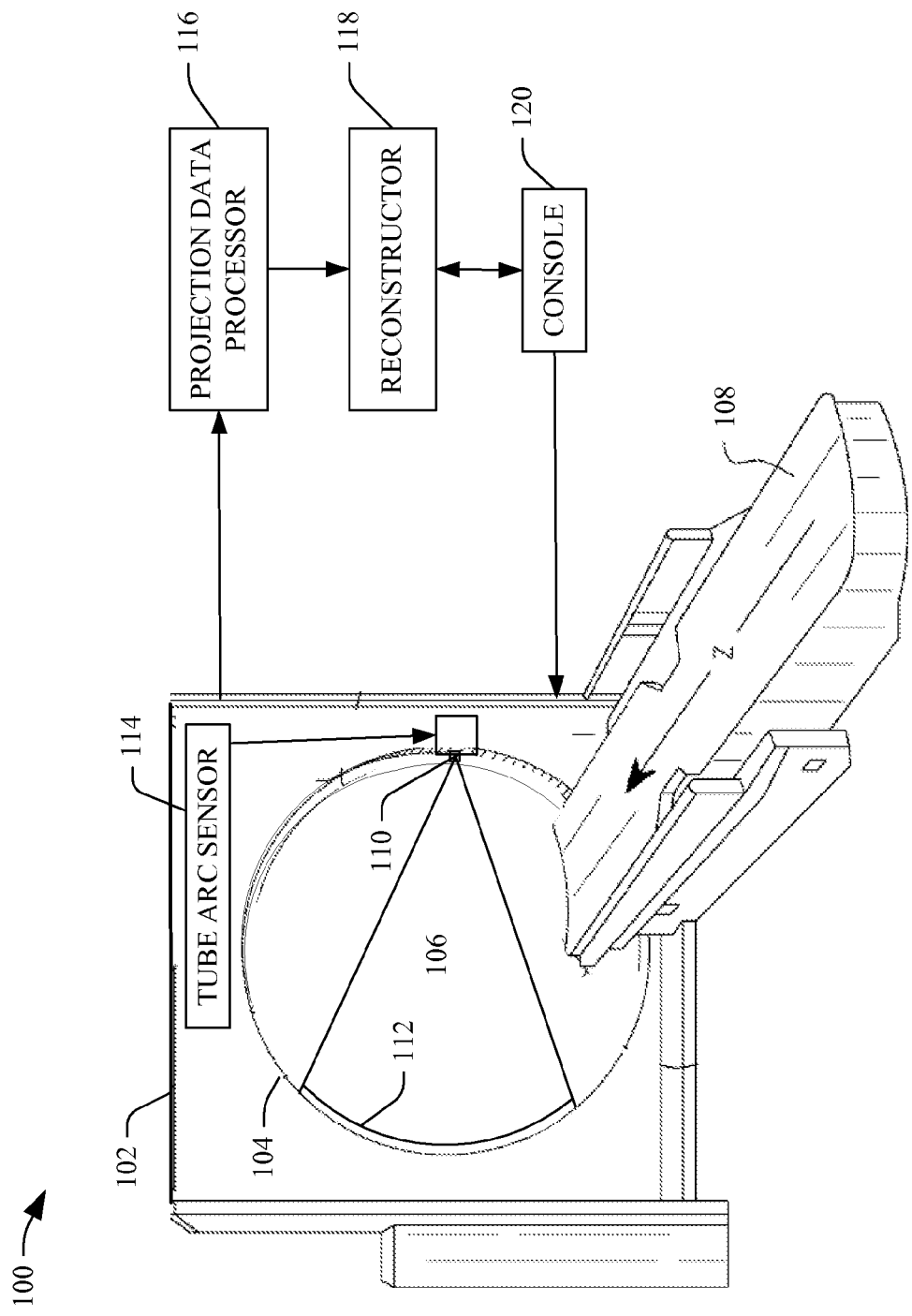
FIG. 1 illustrates an imaging system in connection with a projection data processor.

FIG. 1 illustrates an imaging system 100 such as a computed tomography (CT) scanner. The imaging system 100 includes a stationary gantry 102 and a rotating gantry 104, which is rotatably supported by the stationary gantry 102. The rotating gantry 104 rotates around an examination region 106 about a longitudinal or z-axis. A support 108, such as a couch, supports a subject in the examination region 106 and can be used to position the subject with respect to x, y, and/or z axes before, during and/or after scanning. A radiation source 110, such as an x-ray tube, is supported by the rotating gantry 104 and rotates with the rotating gantry 104 about the examination region 106, and emits radiation that traverses the examination region 106.

A one or two dimensional radiation sensitive detector array 112 is located opposite the radiation source 110, across the examination region 106, and detects radiation that traverses the examination region 106. The detector array 112 generates a signal or projection data indicative of the detected radiation. In the illustrated embodiment, the detector array 112 includes at least two detectors that receive radiation from the source unobstructed by the object or subjected being scanned in the examination region 106. At least one of these detectors includes a filter (e.g., copper) having known spectral characteristics and a known thickness, and at least one of the detectors does not include the filter. As described in greater detail below, the projection data generated by these two detectors can be used to determine the tube voltage for corresponding acquisition intervals.

A tube arc sensor 114 senses x-ray tube arc events and generates a tube arc signal indicative thereof. In one instance, the tube arc signal is a bit that is set when an arc occurs and reset after a pre-determined period of time from the arc at which the high-voltage has recovered back up to a pre-determined level (e.g., 90%). The tube arc signal can be conveyed along with and/or part of the projection data from the detector array 112. A projection data processor 116 processes the projection data. As described in greater detail below, in one instance, the projection data processor 116 corrects at least a sub-set of the projection data generated with data acquired during an x-ray tube arc event. This allows for reducing, if not eliminating, the amount of data that is discarded and created through interpolation in connection with an x-ray tube arc event, which may result in improved image quality.

A reconstructor 118 reconstructs the processed projection data and generates volumetric image data indicative of the examination region 106. The volumetric image data can be processed by an image processor or the like to generate one or more images. A general purpose computing system serves as an operator console 120, and includes an output device such as a display and an input device such as a keyboard, mouse, and/or the like. Software resident on the console 120 allows the operator to control the operation of the system 100, for example, allowing the operator to activate tube arc data correction, initiate scanning, etc.

It is to be appreciated that the projection data processor 116 may be part of the console 120, the reconstructor 118, and/or other computing system such as one or more computers. A suitable computing system includes one or more processors that execute one or more computer readable instructions encoded or embodied in computer readable storage medium such as local, portable, or remote physical memory. Additionally or alternatively, the one or more instructions may be carried by a carrier such as a signal or a wave. The one or more processors, when executing one or more of the instructions, cause the one or more processors to carry out the functionality of the A projection data processor 116 and/or other functionality.

Figure 2:
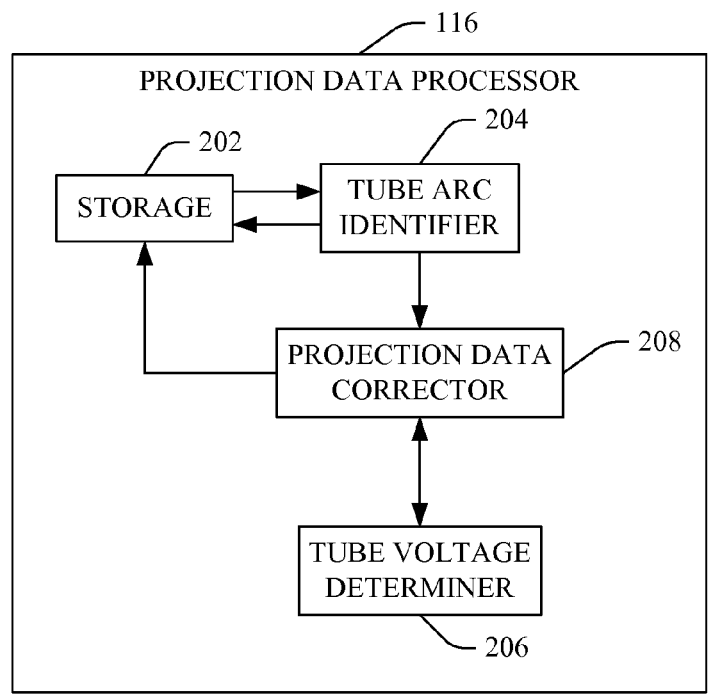
FIG. 2 illustrates an example projection data processor.

FIG. 2 illustrates an example of the projection data processor 116, which corrects the projection data based on the x-ray tube voltage during the arc event.

In the illustrated embodiment, the projection data processor 116 includes storage 202 that stores the projection data and any corrected projection data. In another embodiment, the storage 202 may be external to the data processor 116.

A tube arc identifier 204 evaluates the tube arc bit of the projection data. If the tube arc bit is not set for certain projection data, then that projection data is not processed by the projection data processor. However, if the tube arc bit is set for other projection data, then that this projection data is forwarded for tube arc correction processing.

Figure 3:
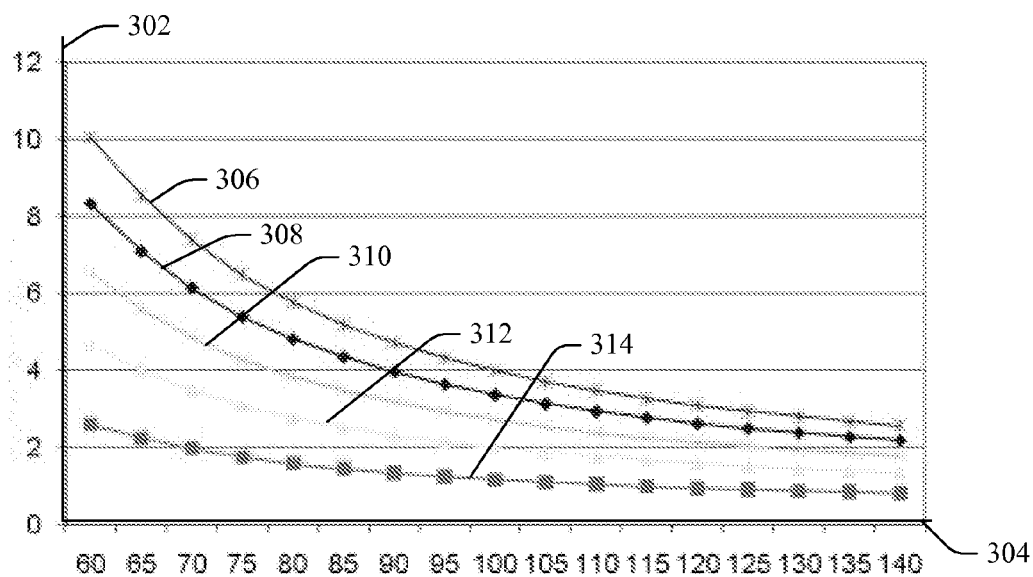
FIG. 3 illustrates an example attenuation-to-voltage mapping.

A tube voltage determiner 206 determines the tube voltage for the projection data to be processed based on the corresponding projection data. In the illustrated embodiment, the tube voltage determiner 206 determines the tube voltage based on a pre-determined attenuation ratio to voltage mapping. FIG. 3 illustrates such a mapping in which a y-axis 302 represents the attenuation ratio and an x-axis 304 represents kV. The illustrated mapping is for tube voltages of 60 kV to 140 kV, and shows five mappings 306, 308, 310, 312, and 314 for five different detector filter differences (e.g., 1 to 5 mm thicknesses in increments of 1 mm). In other embodiment, different voltage ranges, including a lower and/or higher kV, and/or different thicknesses may be used.

The following provides an example for generating the mapping. During a calibration procedure, a ratio of the projection data from the detector with the filter to the projection from the detector without the filter is determined. This ratio is collected at the different voltages for the different filter thickness. A relationship between the attenuation ratio and voltage is then determined and used to populate the graph of FIG. 3. Where the filter utilized with a scanner has a thickness of one of these thicknesses from FIG. 3, then the ratio of the projection data during an arc can be determined by the mapping of the ratio to the voltage based on the filter thickness. Where a different filter thickness is used, the curves of FIG. 3 can be used to derive the voltage via interpolation or extrapolation.

FIG. 3 can be stored as a look up table (LUT) or the like for use by the tube voltage determiner 206. Additionally or alternately, the tube voltage determiner 206 can employ a polynomial equation to convert the projection data ratio to a tube voltage. An example of a polynomial derived from FIG. 3 for one of the thickness is: voltage=$1.7443\mu^2-24.755\mu^3+132.3188\mu^2-327.8174\mu+396.9295$, where $\mu$ represents the projection data ratio. The above approach is provided for explanatory purposes and is not limiting; other approaches are also contemplated herein. For example, in another instance, the kV rise time can be characterized as a function of the kV and mA of the particular technique. The acquisition interval or integration period can be used in conjunction with the rise time profiles to estimate the high-voltage at integration periods before and after the arc-bit transition from the set to non-active state.

A projection data corrector 208 corrects projection data. As briefly discussed above, the projection data corrector 208 corrects projection data based on the tube voltage of the corresponding data acquisition. In this example, the projection data corrector 208 corrects the data as a function of the transformation of EQUATION 1:

$$u_{corrected} = \left(\frac{a}{(kV-b)^{0.5}}\right) + c. \quad \text{EQUATION 1}$$

In this example, a, b, and c are determined in terms of thickness t of the filter material through performing three scans at three known voltages and solving three simultaneous equations. For this example, a, b, and c are derived from water simulations. However, a, b, and c can additionally or alternatively be derived from bone, fat, soft tissue, contrast material and/or other structure.

Figure 4:
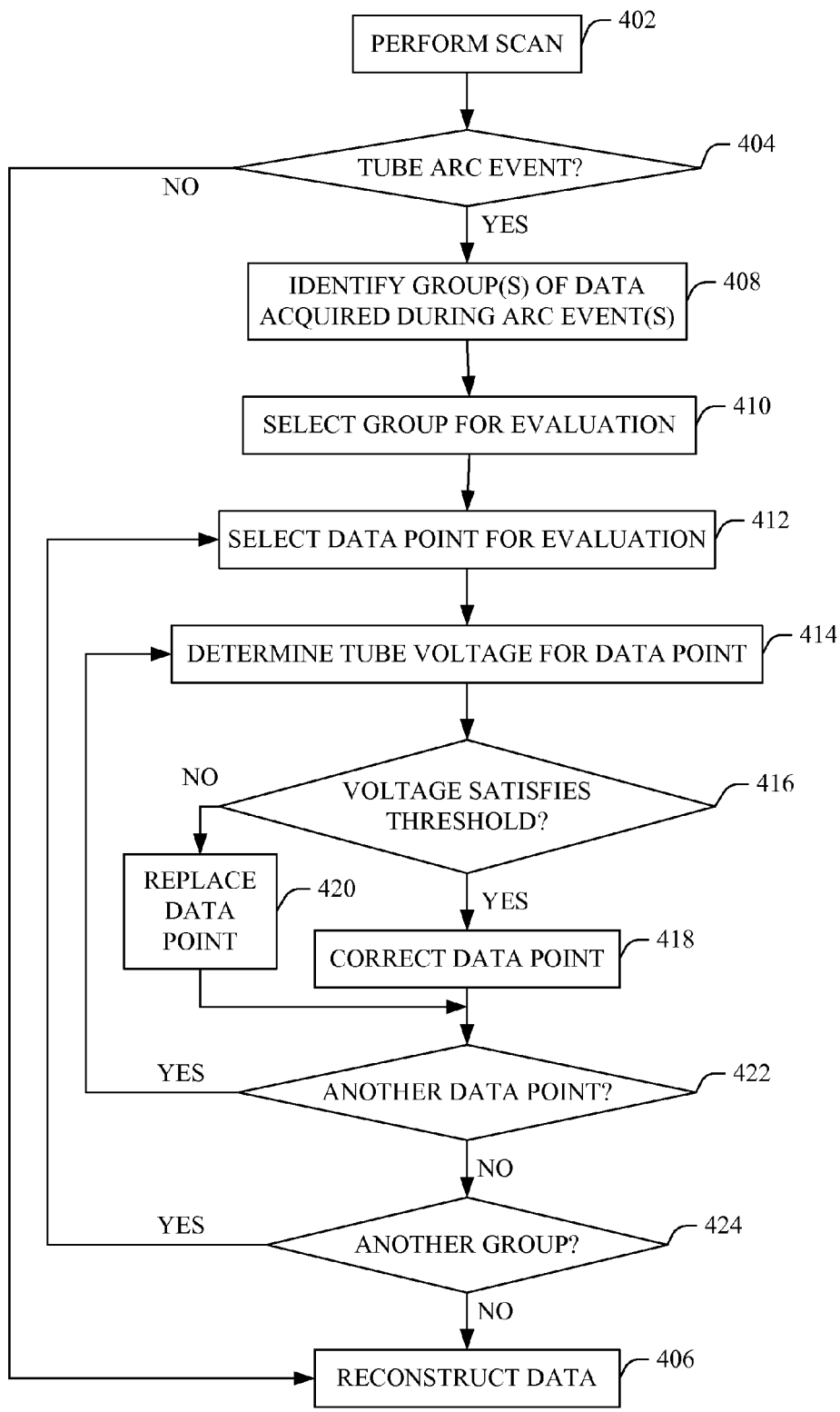
FIG. 4 illustrates an example method.

FIG. 4 illustrates a method for correcting projection data acquired during an x-ray tube arc event.

It is to be appreciated that the ordering of the acts is not limiting. As such, in other embodiments, the ordering of the acts may be different. In addition, one or more of the acts can be omitted and/or one or more other acts can be added.

At 402, a scan is performed.

At 404, it is determined whether there was a tube arc event during the scan. As discussed herein, the state of the tube arc bit can be used to determine whether there was a tube arc event during the scan.

If not, then at 406, the projection data is reconstructed.

If so, then at 408 one or more groups of projection data respectively acquired during one or more x-ray tube arc events are identified.

At 410, one of the groups is selected for evaluation.

At 412, one of the data points of the group is selected for evaluation. In one instance, the selected data point is the last data point of the group. In this instance, the algorithm works backwards in time to correct all of the data points in the group or to correct data points in the group up to a pre-determined threshold such as a tube voltage threshold, a percentage in reduction of tube voltage from the technique nominal threshold, etc.

In another instance, the selected data point is the first data point of the group, and the algorithm is applied sequentially in time, for example, correcting all of the data points in the group successively or moving forward until a data point with a voltage that satisfies a pre-determined threshold such as a tube voltage threshold, a percentage in reduction of tube voltage from the technique nominal threshold, etc. is reached.

In another instance, the selected data point lies between the first and last data, and the correction is performed forwarding looking in time or in both directions. Other approaches are also contemplated herein.

At 414, a tube voltage for the data point is determined. As described herein, the tube voltage can be determined from a look up table, polynomial, or the like generated based on measurements by detectors (at least one with a filter with known spectral characteristics and at least one without such a filter) that directly receive radiation (i.e., the object or subject to be scanned does not lies between the source and the detector).

At 416, it is determined whether the tube voltage for the data point satisfies a predetermined correction threshold voltage. For example, in one instance the correction is only applied if the tube voltage for the data is above a pre-determined voltage such as 60 kV, the tube voltage is no lower than 60% of the nominal technique voltage, and/or other criteria. In another instance, this act is omitted, and data is corrected during the arc event regardless of the tube voltage.

If so, then at 418, the data point is corrected. As described herein, the data can be corrected based on the corresponding tube voltage.

If not, then at 420, the data point is replaced. As described herein, the data can be discarded and replaced with interpolated data. Where act 416 is omitted, act 420 can also be omitted.

At 422, it is determined whether there is another data point in the group for evaluation.

If so, act 414 is repeated for another data point of the group.

If not, then at 424 it is determined whether there is another group to evaluate.

If so, 412 is repeated for the next group.

If not, then at 406, the projection data, which includes original projection data and corrected projection data, is reconstructed.

The above described acts may be implemented by way of computer readable instructions, which, when executed by a computer processor(s), causes the processor(s) to carry out the acts described herein. In such a case, the instructions are stored in a computer readable storage medium such as memory associated with and/or otherwise accessible to the relevant computer.

Figure 5:
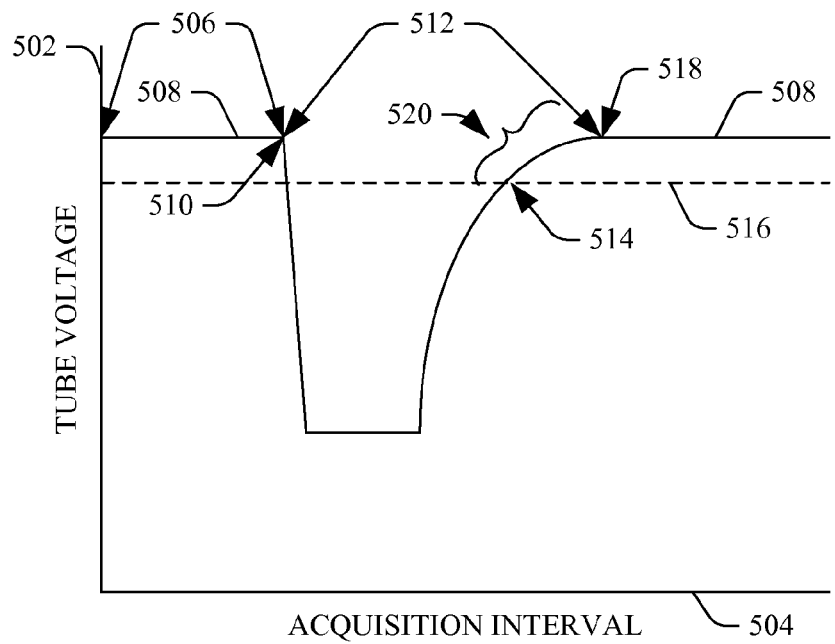
FIG. 5 illustrates a graphical example of the correcting a sub-set of the projection data generated from data acquired during a tube arc event.

FIG. 5 illustrates a graphical example of the correcting a sub-set of the projection data generated from data acquired during a tube arc event. In FIG. 5, the y-axis 502 represents tube voltage and the x-axis 504 represents acquisition interval. During a region 506, the tube voltage is at about a nominal tube voltage 508 of the imaging technique.

At 510, an arc occurs. During a region 512, the tube voltage drops and then recovers based on the rise time of the tube. At 514, the tube voltage has recovered up to a pre-determined voltage threshold 516, and at 518, the tube voltage has recovered up to the nominal tube voltage 508 of the imaging technique.

In this example, the system is configured to correct projection data corresponding to an arc event for data points corresponding to tube voltages greater than the pre-determined voltage threshold 516. As such, the data points in a range 520 from the threshold 516 to the nominal tube voltage 508 are corrected, and the data points from the arc 510 to the threshold are interpolated.

Where the system does not employ the projection data processor 116 the entire range from 510 to 508 is interpolated. As such, the correcting the projection data as described herein at least reduces the amount of data points corresponding to an arc event that are discarded and replaced with interpolated data.

Figure 6:
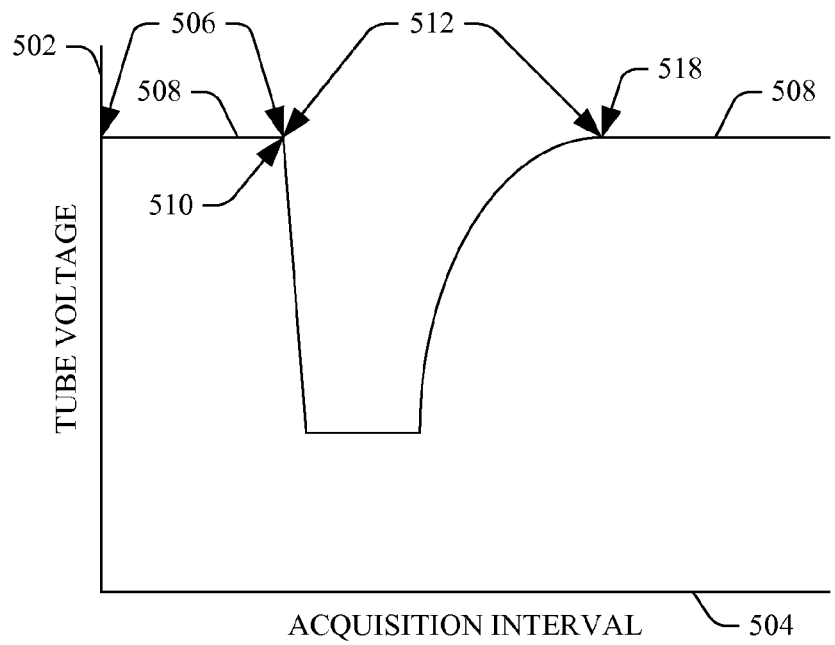
FIG. 6 illustrates a graphical example of the correcting all of projection data generated from data acquired during a tube arc event.

FIG. 6 is similar to FIG. 5 except that the threshold 516 is omitted, and the entire range of data points 512 is corrected, and no data is discarded.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

What is claimed is:

1. A method, comprising:
   (a) detecting unobstructed radiation with a first detector;
   (b) concurrently detecting unobstructed radiation with a second detector,
   wherein the second detector includes a filter material with a known thickness and spectral characteristics and the first detector does not include any filter;
   (c) determining a ratio of output data from the first detector to the second detector;
   performing (a)-(c) for a plurality of known tube voltages; and
   generating a mapping between the ratio and tube voltage as a function of the tube voltages;
   identifying projection data generated during an x-ray tube arc event;
   determining x-ray tube voltages for data points of the identified projection data, wherein determining the x-ray tube voltages for the data points includes determining the x-ray tube voltages based on the mapping;
   correcting the identified data points based on the determined x-ray tube voltages for the data points, wherein the data points are corrected based on the following transformation:

$$u_{corrected} = \left(\frac{a}{(kV-b)^{0.5}}\right) + c$$

where $u_{corrected}$ is the corrected projection data, kV is the determined x-ray tube voltage and a, b and c are constants in units of a thickness of the filter material determined by performing three scans at three known voltages and solving three simultaneous equations;
   reconstructing projection data that includes projection data generated during non x-ray tube arc events and the corrected projection data, which generates volumetric image data; and
   displaying on a display unit the volumetric image data generated by reconstructing the projection data that includes the projection data generated during non x-ray tube arc events and the corrected projection data.

2. The method of claim 1, further comprising:
   comparing the determined x-ray tube voltage for a data point with a predetermined correction threshold voltage;
   determining whether the determined x-ray tube voltage satisfies the predetermined correction threshold voltage; and
   correcting the data point in response to the tube voltage satisfying the predetermined correction threshold voltage.

3. The method of claim 2, further comprising:
replacing the data point with a derived data point in response to the tube voltage not satisfying the predetermined correction threshold voltage.

4. The method of claim 2, wherein the predetermined correction threshold voltage is about 60 kV or 60% of a nominal voltage of a scan emission voltage.

5. The method of claim 1, further comprising:
determining the ratio for the data points; and
determining the x-ray tube voltages for the data points based on the determined ratios and the mapping.

6. The method of claim 1, wherein the mapping is stored in a look up table.

7. The method of claim 1, wherein the mapping is expressed as a polynomial.

8. The method of claim 1, wherein the data points are corrected as a function of determined tube voltage and the thickness of the filter material.

9. A system, comprising:
a projection data processor that corrects projection data corresponding to data acquired during an x-ray tube arc event based on the following transformation:

$$u_{corrected} = \left(\frac{a}{(kV-b)^{0.5}}\right) + c$$

where $u_{corrected}$ is corrected projection data, kV is an x-ray tube voltage, and a, b and c are constants in units of a thickness of a filter material determined by performing three scans at three known voltages and solving three simultaneous equations;
a reconstructor that reconstructs projection data that includes projection data generated during non x-ray tube arc events and the corrected projection data which generates volumetric image data and
a display unit that displays the volumetric image data generated by reconstructing the projection data that includes the projection data generated during non x-ray tube arc events and the corrected projection data.

10. The system of claim 9, the projection data processor, comprising:
a tube arc identifier that identifies one or more groups of the projection data that correspond to the data acquired during the x-ray tube arc event.

11. The system of claim 10, the projection data processor, comprising:
a tube voltage determiner that determines x-ray tube voltages respectively for data points of the one or more identified groups.

12. The system of claim 11, the projection data processor, comprising:
a projection data correction that corrects at least a sub-set of the data points based on the corresponding determined x-ray tube voltages.

13. The system of claim 12, wherein data points that are not corrected are replaced with interpolated data points.

14. The system of claim 12, wherein the projection data correction corrects the data points backwards in time in a direction from a last of the data points to a first of the data points.

15. The system of claim 12, wherein the projection data correction corrects the data points sequentially based on acquisition time.

16. The system of claim 9, wherein a set of projection data that includes projection data generated during non x-ray tube arc events and the corrected projection data is reconstructed to generate volumetric image data.

17. A method of correcting data collected during an x-ray tube arc, comprising:
identifying the tube arc;
establishing a relationship between x-ray attenuation values and x-ray tube voltage;
determining one or more x-ray tube voltages at different time periods during the tube arc;
correcting the x-ray attenuation values based on the following transformation:

$$u_{corrected} = \left(\frac{a}{(kV-b)^{0.5}}\right) + c$$

where $u_{corrected}$ is corrected projection data, kV is the one or more x-ray tube voltages, and a, b and c are constants in units of a thickness of the filter material determined by performing three scans at three known voltages and solving three simultaneous equations;
reconstructing projection data that includes projection data generated during non x-ray tube arc events and the corrected projection data, which generates volumetric image data: and
displaying on a display unit the volumetric image data generated by reconstructing the projection data that includes the projection data generated during non x-ray tube arc events and the corrected projection data.

* * * * *